(12) United States Patent
Bai et al.

(10) Patent No.: US 6,881,835 B2
(45) Date of Patent: Apr. 19, 2005

(54) DETECTION OF RESPIRATORY VIRUSES

(75) Inventors: Yue-Luen Bai, Hsinchu (TW); Harn-Jing Terng, Hsinchu (TW)

(73) Assignee: Dr. Chip Biotechnology Inc., Hsinchu (TW)

( * ) Notice: Subject to any disclaimer, the term of this patent is extended or adjusted under 35 U.S.C. 154(b) by 0 days.

(21) Appl. No.: 10/038,835

(22) Filed: Jan. 4, 2002

(65) Prior Publication Data

US 2003/0130497 A1 Jul. 10, 2003

(51) Int. Cl.[7] .......................... C07H 21/02; C12Q 1/68
(52) U.S. Cl. ................ 536/24.3; 536/23.1; 536/24.31; 536/24.32; 536/24.33; 435/6
(58) Field of Search ................. 536/23.1, 24.3, 536/24.31, 24.32, 24.33; 435/5, 6

(56) References Cited

U.S. PATENT DOCUMENTS

| | | | |
|---|---|---|---|
| 5,187,060 A | 2/1993 | Cerutti et al. ................ 435/5 |
| 5,374,717 A | * 12/1994 | Rota et al. ............... 536/23.72 |
| 5,401,626 A | 3/1995 | Kondo et al. ................. 435/5 |
| 5,744,299 A | 4/1998 | Henrickson et al. .......... 435/5 |
| 6,015,664 A | 1/2000 | Henrickson et al. .......... 435/5 |

FOREIGN PATENT DOCUMENTS

| | | | |
|---|---|---|---|
| WO | WO 00/17391 | 3/2000 | ............ C12Q/1/68 |

OTHER PUBLICATIONS

Genbank Accession No. X55803 (May 4, 1993).*
Genbank Accessiion No. X57559 (May 13, 1992).*
Genbank Accession No. M18759 (Aug. 2, 1993).*
Genbank Accession No. M73260 (Apr. 8, 1996).*
Grondahl et al, "Rapid identification of nine microorganisms causing acute respiratory tract infections by single tube multiplex reverse transcription PCR: feasibility study", J. Clin. Microbiol. (1999) 37:1–7.*
Echevarria et al, "Simultaneous detection and identification of human parainfluenza viruses 1, 2 and 3 from clinical samples by multiplex PCR," J. Clin. Microbiol. (1998) 36:1388–1391).*
Osiowy et al, "Direct detection of respiratory syncytial virus, parainfluenza virus and adenovirus in clinical respiratory specimens by a multiplex reverse transcription–PCR assay", J. Clin. Microbiol. (1998) 36:3149–3154.*
Zuckerman et al, "Direct sequence determination of the influenza B HA–1 gene after PCR amplification of clinical specimens from an infected volunteer", J. Virol. Meth. (1993) 44:35–44.*
Genbank Accession No. M11486 (Nov. 29, 2000).*
Genbank Accession No. M12594 (Aug. 2, 1993).*
Ikeda et al, "Genome types of Adenovirus TYpe 7 Isolated in Hiroshima City", J. Med. Virol. (2003) 69:215–219.*
Buck et al, "Design strategies and performance of custom DNA sequencing primers", Biotechniques (1999) 27:528–536.*

* cited by examiner

*Primary Examiner*—Jeffrey Fredman
(74) *Attorney, Agent, or Firm*—Fish & Richardson P.C.

(57) ABSTRACT

Specific nucleic acid sequences, e.g., SEQ ID NOs:1–57, for simultaneous detection of seven most common viruses that cause respiratory infections in human, i.e., human parainfluenza virus 1, human parainfluenza virus 2, human parainfluenza virus 3, respiratory syncytial virus, influenza virus A, influenza virus B, and adenovirus. Also disclosed is a method of simultaneously detecting these viruses. The method includes providing a nucleic acid prepared from a sample suspected of containing a virus to be detected, amplifying the nucleic acid with a set of primers specific for one or more of the seven viruses, and detecting amplification products. Detection of an amplification product specific for any one of the seven viruses indicates the presence of that particular virus.

6 Claims, No Drawings

SEQUENCE LISTING

<160> NUMBER OF SEQ ID NOS: 57

<210> SEQ ID NO 1
<211> LENGTH: 22
<212> TYPE: DNA
<213> ORGANISM: Human parainfluenza virus 1

<400> SEQUENCE: 1
ctgtaatagc tgcaggaaca ag                                           22

<210> SEQ ID NO 2
<211> LENGTH: 23
<212> TYPE: DNA
<213> ORGANISM: Human parainfluenza virus 1

<400> SEQUENCE: 2 acaagggggtt atcagttatg ctc                                         23

<210> SEQ ID NO 3
<211> LENGTH: 24
<212> TYPE: DNA
<213> ORGANISM: Human parainfluenza virus 1

<400> SEQUENCE: 3
ttcaatyttt atcccrcttc ctac                                         24

<210> SEQ ID NO 4
<211> LENGTH: 19
<212> TYPE: DNA
<213> ORGANISM: Human parainfluenza virus 1

<400> SEQUENCE: 4
ccttggagcg gagttgtta                                               19

<210> SEQ ID NO 5
<211> LENGTH: 22
<212> TYPE: DNA
<213> ORGANISM: Human parainfluenza virus 2

<400> SEQUENCE: 5
gctgttcagt cactgctata cc                                           22

<210> SEQ ID NO 6
<211> LENGTH: 23
<212> TYPE: DNA
<213> ORGANISM: Human parainfluenza virus 2

<400> SEQUENCE: 6
gatctagctg aactgagact tgc                                          23

```
<210> SEQ ID NO 7
<211> LENGTH: 24
<212> TYPE: DNA
<213> ORGANISM: Human parainfluenza virus 2

<400> SEQUENCE: 7
tatgagacca ccatatacag gaaa                                              24

<210> SEQ ID NO 8
<211> LENGTH: 24
<212> TYPE: DNA
<213> ORGANISM: Human parainfluenza virus 3

<400> SEQUENCE: 8
ctgtaaactc agacttggta cctg                                              24

<210> SEQ ID NO 9
<211> LENGTH: 24
<212> TYPE: DNA
<213> ORGANISM: Human parainfluenza virus 3

<400> SEQUENCE: 9
agttgatgaa agatcagatt atgc                                              24

<210> SEQ ID NO 10
<211> LENGTH: 26
<212> TYPE: DNA
<213> ORGANISM: Human parainfluenza virus 3

<400> SEQUENCE: 10
atatcaagta caatatcttc tatgcc                                            26

<210> SEQ ID NO 11
<211> LENGTH: 21
<212> TYPE: DNA
<213> ORGANISM: Human parainfluenza virus 3

<400> SEQUENCE: 11
cctggtccaa cagatgggta t                                                 21

<210> SEQ ID NO 12
<211> LENGTH: 21
<212> TYPE: DNA
<213> ORGANISM: Human respiratory syncytial virus

<400> SEQUENCE: 12
gyattggcat taagcctaca a                                                 21

<210> SEQ ID NO 13
<211> LENGTH: 24
<212> TYPE: DNA
<213> ORGANISM: Human respiratory syncytial virus

<400> SEQUENCE: 13
ggattgttta tgaatgccta tggt                                              24

<210> SEQ ID NO 14
<211> LENGTH: 23
<212> TYPE: DNA
<213> ORGANISM: Human respiratory syncytial virus

<400> SEQUENCE: 14
aacttgactt tgctaagagc cat                                               23
```

```
<210> SEQ ID NO 15
<211> LENGTH: 24
<212> TYPE: DNA
<213> ORGANISM: Human respiratory syncytial virus

<400> SEQUENCE: 15
ttggrttgtt caatatatgg taga                                              24

<210> SEQ ID NO 16
<211> LENGTH: 22
<212> TYPE: DNA
<213> ORGANISM: Influenzavirus A

<400> SEQUENCE: 16
cacttaaaat gaccatggcc tc                                                22

<210> SEQ ID NO 17
<211> LENGTH: 21
<212> TYPE: DNA
<213> ORGANISM: Influenzavirus A

<400> SEQUENCE: 17
cgaaatttca ccattgcctt c                                                 21

<210> SEQ ID NO 18
<211> LENGTH: 22
<212> TYPE: DNA
<213> ORGANISM: Influenzavirus A

<400> SEQUENCE: 18
gaaggcttag gtgaaatttc gc                                                22

<210> SEQ ID NO 19
<211> LENGTH: 22
<212> TYPE: DNA
<213> ORGANISM: Influenzavirus A

<400> SEQUENCE: 19
gtctcacttc ttcaatcagc ca                                                22

<210> SEQ ID NO 20
<211> LENGTH: 22
<212> TYPE: DNA
<213> ORGANISM: Influenzavirus B

<400> SEQUENCE: 20
ctgggataac atcktcaaac tc                                                22

<210> SEQ ID NO 21
<211> LENGTH: 17
<212> TYPE: DNA
<213> ORGANISM: Influenzavirus B

<400> SEQUENCE: 21
aacaatggct tgggctg                                                      17

<210> SEQ ID NO 22
<211> LENGTH: 21
<212> TYPE: DNA
<213> ORGANISM: Influenzavirus B

<400> SEQUENCE: 22
tgttctgtcg tgcattatag g                                                 21
```

```
<210> SEQ ID NO 23
<211> LENGTH: 18
<212> TYPE: DNA
<213> ORGANISM: Influenzavirus B

<400> SEQUENCE: 23
caacaattct rccgcttt                                              18

<210> SEQ ID NO 24
<211> LENGTH: 16
<212> TYPE: DNA
<213> ORGANISM: Human adenovirus type 1

<400> SEQUENCE: 24
ccaccttctt ccccat                                                16

<210> SEQ ID NO 25
<211> LENGTH: 19
<212> TYPE: DNA
<213> ORGANISM: Human adenovirus type 1

<400> SEQUENCE: 25
aacatgacca argactggt                                             19

<210> SEQ ID NO 26
<211> LENGTH: 17
<212> TYPE: DNA
<213> ORGANISM: Human adenovirus type 1

<400> SEQUENCE: 26
ctcatkggct ggaagtt                                               17

<210> SEQ ID NO 27
<211> LENGTH: 20
<212> TYPE: DNA
<213> ORGANISM: Human adenovirus type 1

<400> SEQUENCE: 27
gaaccagtcy ttggtcatgt                                            20

<210> SEQ ID NO 28
<211> LENGTH: 26
<212> TYPE: DNA
<213> ORGANISM: Human parainfluenza virus 1

<400> SEQUENCE: 28
ctccytgccy actgtraatg agacta                                     26

<210> SEQ ID NO 29
<211> LENGTH: 33
<212> TYPE: DNA
<213> ORGANISM: Human parainfluenza virus 1

<400> SEQUENCE: 29
cgagtgaagg tatagaagay ttagtatttg aca                             33

<210> SEQ ID NO 30
<211> LENGTH: 26
<212> TYPE: DNA
<213> ORGANISM: Human parainfluenza virus 1

<400> SEQUENCE: 30
```

```
ctcaagggaa agaccaaatc tcatcg                                          26
```

<210> SEQ ID NO 31
<211> LENGTH: 30
<212> TYPE: DNA
<213> ORGANISM: Human parainfluenza virus 1

<400> SEQUENCE: 31

```
gctgcaggaa caagggggtta tcagttatgc                                     30
```

<210> SEQ ID NO 32
<211> LENGTH: 26
<212> TYPE: DNA
<213> ORGANISM: Human parainfluenza virus 1

<400> SEQUENCE: 32

```
gtgtaggaag rgggataaay attgaa                                          26
```

<210> SEQ ID NO 33
<211> LENGTH: 27
<212> TYPE: DNA
<213> ORGANISM: Human parainfluenza virus 1

<400> SEQUENCE: 33

```
ccttggagcg gagttgttaa gccaccg                                         27
```

<210> SEQ ID NO 34
<211> LENGTH: 36
<212> TYPE: DNA
<213> ORGANISM: Human parainfluenza virus 2

<400> SEQUENCE: 34

```
gatctagctg aactgagact tgctttctat tattat                               36
```

<210> SEQ ID NO 35
<211> LENGTH: 28
<212> TYPE: DNA
<213> ORGANISM: Human parainfluenza virus 2

<400> SEQUENCE: 35

```
tcatatctct tccaaayaca acagggca                                        28
```

<210> SEQ ID NO 36
<211> LENGTH: 23
<212> TYPE: DNA
<213> ORGANISM: Human parainfluenza virus 2

<400> SEQUENCE: 36

```
tgcagtygga agcgggatct atc                                             23
```

<210> SEQ ID NO 37
<211> LENGTH: 29
<212> TYPE: DNA
<213> ORGANISM: Human parainfluenza virus 3

<400> SEQUENCE: 37

```
tgcatcatca ggcatagaag atattgtac                                       29
```

<210> SEQ ID NO 38
<211> LENGTH: 28
<212> TYPE: DNA
<213> ORGANISM: Human parainfluenza virus 3

<400> SEQUENCE: 38

-continued atyatgatgg ytcaatctca acaacaag                28

<210> SEQ ID NO 39
<211> LENGTH: 34
<212> TYPE: DNA
<213> ORGANISM: Human parainfluenza virus 3

<400> SEQUENCE: 39
atctcaacaa caagatttaa gaayaataay ataa          34

<210> SEQ ID NO 40
<211> LENGTH: 28
<212> TYPE: DNA
<213> ORGANISM: Respiratory syncytial virus

<400> SEQUENCE: 40
taagcctaca aagcayactc ccataata                 28

<210> SEQ ID NO 41
<211> LENGTH: 28
<212> TYPE: DNA
<213> ORGANISM: Respiratory syncytial virus

<400> SEQUENCE: 41
aaatatgacc tcaacccgta aattccaa                 28

<210> SEQ ID NO 42
<211> LENGTH: 24
<212> TYPE: DNA
<213> ORGANISM: Respiratory syncytial virus

<400> SEQUENCE: 42
aacccawcca aacyaagcta ttcc                     24

<210> SEQ ID NO 43
<211> LENGTH: 39
<212> TYPE: DNA
<213> ORGANISM: Respiratory syncytial virus

<400> SEQUENCE: 43
gatggagcct gaaaattata gtaatttaaa attaaggag     39

<210> SEQ ID NO 44
<211> LENGTH: 30
<212> TYPE: DNA
<213> ORGANISM: Respiratory syncytial virus

<400> SEQUENCE: 44
caaacaacar tgctcaayag ttaagaagga              30

<210> SEQ ID NO 45
<211> LENGTH: 28
<212> TYPE: DNA
<213> ORGANISM: Respiratory syncytial virus

<400> SEQUENCE: 45
aggagagata taagatgaaa gatggggc                 28

<210> SEQ ID NO 46
<211> LENGTH: 28
<212> TYPE: DNA
<213> ORGANISM: Respiratory syncytial virus

```
<400> SEQUENCE: 46
aggagagaca taagatagaa gatggggc                                          28

<210> SEQ ID NO 47
<211> LENGTH: 27
<212> TYPE: DNA
<213> ORGANISM: Influenzavirus A

<400> SEQUENCE: 47
cggaggactt gaatggartg ataacac                                           27

<210> SEQ ID NO 48
<211> LENGTH: 27
<212> TYPE: DNA
<213> ORGANISM: Influenzavirus A

<400> SEQUENCE: 48
tctacagaga ttcgcttggr gaagcag                                           27

<210> SEQ ID NO 49
<211> LENGTH: 27
<212> TYPE: DNA
<213> ORGANISM: Influenzavirus A

<400> SEQUENCE: 49
gacmtccact yactccaaaa cagaaac                                           27

<210> SEQ ID NO 50
<211> LENGTH: 27
<212> TYPE: DNA
<213> ORGANISM: Influenzavirus B

<400> SEQUENCE: 50
tgtgatacca ctgacaacaa caccwac                                           27

<210> SEQ ID NO 51
<211> LENGTH: 26
<212> TYPE: DNA
<213> ORGANISM: Influenzavirus B

<400> SEQUENCE: 51
gcaaatctca aaggaacaaa racyag                                            26

<210> SEQ ID NO 52
<211> LENGTH: 27
<212> TYPE: DNA
<213> ORGANISM: Influenzavirus B

<400> SEQUENCE: 52
aaactatgcc caamstgtyt caactgy                                           27

<210> SEQ ID NO 53
<211> LENGTH: 22
<212> TYPE: DNA
<213> ORGANISM: Human adenovirus
<220> FEATURE:
<221> NAME/KEY: misc_feature
<222> LOCATION: (1)...(22)
<223> OTHER INFORMATION: n = A,T,C or G

<400> SEQUENCE: 53
tccccatggc bcacaacacn gc                                                22
```

-continued

```
<210> SEQ ID NO 54
<211> LENGTH: 20
<212> TYPE: DNA
<213> ORGANISM: Human adenovirus

<400> SEQUENCE: 54
tckcgcaact gggcrgcytt                                                    20

<210> SEQ ID NO 55
<211> LENGTH: 27
<212> TYPE: DNA
<213> ORGANISM: Human adenovirus

<400> SEQUENCE: 55
aaccacacyt tyaagaaggt skccatc                                            27

<210> SEQ ID NO 56
<211> LENGTH: 26
<212> TYPE: DNA
<213> ORGANISM: Human adenovirus

<400> SEQUENCE: 56
aacatgacca argactggtt cctggt                                             26

<210> SEQ ID NO 57
<211> LENGTH: 26
<212> TYPE: DNA
<213> ORGANISM: Human adenovirus

<400> SEQUENCE: 57
tacaayatyg gmtaccaggg cttyta                                             26
```

DETECTION OF RESPIRATORY VIRUSES

BACKGROUND

Respiratory tract infections cause nearly half of the deaths due to infectious diseases in the United States (Wei, et al., Obstet Gynecol Clin North Am (2001) 28 (2): 283–304). About 75 percent of acute respiratory illnesses are caused by viruses. Human parainfluenza virus 1, human parainfluenza virus 2, human parainfluenza virus 3, respiratory syncytial virus, influenza virus A, influenza virus B, and adenovirus are the most common viruses that cause respiratory infections in both children and adults. Detection of these viruses is essential for diagnosis, prevention and treatment of respiratory diseases.

SUMMARY

The present invention relates to specific nucleic acid sequences for simultaneously detecting multiple respiratory viruses including human parainfluenza virus 1, human parainfluenza virus 2, human parainfluenza virus 3, respiratory syncytial virus, influenza virus A, influenza virus B, and adenovirus.

In one aspect, this invention features a PCR primer set that contains two primer pairs for detecting two respiratory viruses, human parainfluenza virus 2 and adenovirus. One of the human parainfluenza virus 2 primers contains an oligo-nucleotide selected from the hemagglutinin-neuraminidase gene region (e.g., SEQ ID NO:5 or 6), and the other primer contains another oligo-nucleotide also selected from the same region (e.g., SEQ ID NO:7). One of the adenovirus primers contains an oligo-nucleotide selected from the hexon gene region, and the other primer contains another oligo-nucleotide also selected from the same region. For example, the oligo-nucleotides in an adenovirus primer pair can be, SEQ ID NOs:24 and 26, SEQ ID NOs:24 and 27, or SEQ ID NOs:25 and 27. Each oligo-nucleotide has 14–40 (e.g., 14–35, 14–30, 14–25, or 14–20) nucleotides in length.

The PCR primer set of this invention can further contain one or more additional specific primer pairs for detecting other respiratory viruses. For instance, one or more of the following five primer pairs (including any combination thereof) can be included in the PCR primer set:

(1) a pair of human parainfluenza virus 1 primers, each containing an oligo-nucleotide selected from the hemagglutinin-neuraminidase gene region. For example, the oligo-nucleotides in a human parainfluenza virus 1 primer pair can be, respectively, SEQ ID NOS:1 and 3, SEQ ID NOs:2 and 3, or SEQ ID NOs:1 and 4.

(2) a pair of human parainfluenza virus 3 primers, each containing an oligo-nucleotide selected from the hemagglutinin-neuraminidase gene region. For example, the oligo-nucleotides in a human parainfluenza virus 3 primer pair can be, respectively, SEQ ID NOs:8 and 10, SEQ ID NOs:8 and 11, or SEQ IN NOs:9 and 11.

(3) a pair of respiratory syncytial virus primers, each containing an oligo-nucleotide selected from the non-structural protein 2 gene region. For example, the oligo-nucleotides in a respiratory syncytial virus primer pair can be, respectively, SEQ ID NOS:12 and 14, or SEQ ID 10 NOs:13 and 15.

(4) a pair of influenza virus A primers, each containing an oligo-nucleotide selected from the non-structural protein gene region. For example, the oligo-nucleotides in an influenza virus A primer pair can be, respectively, SEQ ID NOS:16 and 18, or SEQ ID NOS:17 and 19.

(5) a pair of influenza virus B primers selected from the hemagglutinin gene region. For example, the oligo-nucleotides in an influenza virus B primer pair can be, respectively, SEQ ID NO:20 and 22, or SEQ ID NOs:21 and 23.

In another aspect, this invention features a set of nucleic acids that contains one or more nucleic acids obtained from amplification of a group of respiratory virus nucleic acid templates with one of the PCR primer sets described above. The group of nucleic acid templates is prepared from one or more of the seven viruses mentioned above. The amplification products can be used as hybridization probes for virus detection.

In yet another aspect, this invention features a probe set that can be used for detecting the seven respiratory viruses mentioned above. Each probe has 20–1,000 (e.g., 20–500, 20–200, or 20–50) nucleotides in length. The probe set contains one or more of the following:

(1) a respiratory syncytial virus probe including an oligo-nucleotide selected from the non-structural protein 2 gene region. For example, the oligo-nucleotide can be one of SEQ ID NOs:40–46 or its complementary sequence.

(2) an influenza virus A probe including an oligo-nucleotide selected from the non-structural protein gene region. For example, the oligo-nucleotide can be one of SEQ ID NOs: 47–49 or its complementary sequence.

(3) an influenza virus B probe including an oligo-nucleotide selected from the hemagglutinin gene region. For example, the oligo-nucleotide can be one of SEQ ID NOs:50–52 or its complementary sequence.

The probe set of this invention can further contain one or more of the following:

(1) a human parainfluenza virus 1 probe, e.g., a probe including one of oligo-nucleotides SEQ ID NOs:28–33 or its complementary sequence.

(2) a human parainfluenza virus 2 probe, e.g., a probe including one of oligo-nucleotides SEQ ID NOs:34–36 or its complementary sequence.

(3) a human parainfluenza virus 3 probe, e.g., a probe including one of oligo-nucleotides SEQ ID NOs:37–39 or its complementary sequence.

(4) an adenovirus probe, e.g., a probe including one of oligo-nucleotides SEQ ID NOs: 53–57 or its complementary sequences.

Also within the scope of this invention is a method of simultaneously detecting respiratory viruses using a PCR primer set, a set of amplified nucleic acids, or a probe set described above. Among the viruses to be detected are human parainfluenza virus 2 and adenovirus, and optionally, one or more of the following: human parainfluenza virus 1, human parainfluenza virus 3, respiratory syncytial virus, influenza virus A, and influenza virus B. The method includes (1) providing a nucleic acid from a sample suspected of containing a virus to be detected, (2) amplifying the nucleic acid with one of the PCR primer sets described above, and (3) detecting amplification products. Detection of an amplification product specific for a target virus indicates the presence of the target virus, and can be achieved by hybridizing the amplification products to one of the probe sets described above.

Further within the scope of this invention is a kit for simultaneous detection of respiratory viruses including human parainfluenza virus 2 and adenovirus, and optionally, one or more of the following: human parainfluenza virus 1, human parainfluenza virus 3, respiratory syncytial virus, influenza virus A, and influenza virus B. The kit contains a PCR primer set, a set of amplified nucleic acids, a probe set described above, or any combination thereof. It may include other components such as a DNA polymerase, a PCR buffer, or a solid support on which one or more specific probes are immobilized.

The present invention enables one to simultaneously detect as many as seven common respiratory viruses. The details of one or more embodiments of the invention are set forth in the accompanying description below. Other advantages, features, and objects of the invention will be apparent from the description, and from the claims.

DETAILED DESCRIPTION

The present invention relates to simultaneous detection of two respiratory viruses, human parainfluenza virus 2 and adenovirus. Specifically, a nucleic acid template prepared from a sample suspected of containing human parainfluenza virus 2 or adenovirus is amplified with a set of PCR primers, which contains a pair of human parainfluenza virus 2 primers and a pair of adenovirus primers. The amplification product, if any, is detected by either gel electrophoresis and staining, or by probe hybridization. Detection of an amplification product specific for human parainfluenza virus 2 or adenovirus indicates the presence of that virus in the sample. Optionally, the set of PCR primers can contain one or more additional primer pairs for detecting other respiratory viruses such as human parainfluenza virus 1, human parainfluenza virus 3, respiratory syncytial virus, influenza virus A, and influenza virus B.

The nucleic acid template can be DNA (e.g., a genomic fragment or a restriction fragment) or RNA, in a purified or unpurified form. It can also be obtained from a biological sample, e.g., a specimen from a patient having symptoms of respiratory infection.

The present invention features PCR primer pairs which can be used for simultaneously detecting the seven respiratory viruses mentioned above. The primer pairs for each virus are selected by analyzing virus sequences in GenBank using the DNAstar program (DNASTAR Inc., Madison, Wis. 53715, U.S.A.). A conserved region is first identified, followed by selection of primer pairs from this region. Each primer pair can be tested in a PCR using a nucleic acid template prepared from a patient diagnosed with infection of a virus to be detected to ensure that a specific amplification product is produced. When a primer pair is combined with other primer pairs for simultaneous detection of multiple viruses, the specificity of the primer pair should not be affected by the presence of other primer pairs, i.e., the same amplification product is produced. Further, a primer pair selected for one virus preferably does not cause non-specific amplification of a nucleic acid template prepared from another virus, and amplification products specific for different viruses should be of different lengths.

Examples of PCR primer pairs which can be used for simultaneously detecting the seven respiratory viruses mentioned above are as follows:

(1) human parainfluenza virus 1 primer pairs selected from a conserved hemagglutinin-neuraminidase gene region. For example, forward primer PIV1-f834 and reverse primer PIV1-r1049, forward primer PIV1-f849 and reverse primer PIV1-r1049, and forward primer PIV1-f834 and reverse primer PIV1-r1099.

(2) human parainfluenza virus 2 primer pairs selected from a conserved hemagglutinin-neuraminidase gene region. For example, forward primer PIV2-f929 and reverse primer PIV2-r1182, and forward primer PIV2-f1015 and reverse primer PIV2-r1182.

(3) human parainfluenza virus 3 primer pairs selected from a conserved hemagglutinin-neuraminidase gene region. For example, forward primer PIV3-f774 and reverse primer PIV3-r960, forward primer PIV3-f774 and reverse primer PIV3-r1059, and forward primer PIV3-f904 and reverse primer PIV3-r1059.

(4) respiratory syncytial virus primer pairs selected from a conserved non-structural protein 2 gene region. For example, forward primer RSV-f417 and reverse primer RSV-r641, and forward primer RSV-f1351 and reverse primer RSV-r1540.

(5) influenza virus A primer pairs selected from a conserved non-structural protein gene region. For example, forward primer INFA-f1 and reverse primer INFA-r1, forward primer INFA-f2 and reverse primer INFA-r2, and forward primer INFA-f1 and reverse primer INFA-r2.

(6) influenza virus B primer pairs selected from a conserved hemagglutinin protein gene region. For example, forward primer INFB-92f and reverse primer INFB-384r, and forward primer INFB-540f and reverse primer INFB-820r.

(7) adenovirus primer pairs selected from a conserved Hexon protein gene region. For example, forward primer ADV-f1 and reverse primer ADV-r2, and forward primer ADV-f2 and reverse primer ADV-r1.

The sequence of each primer is listed in Table 1 below in Example 1. Typically, a primer is 14–40 nucleotides in length (PCR Application Manual, Boehringer Mannheim, 1995, page 37). In this invention, specific virus sequences can be added to either the 5'-end or the 3'-end of each primer; non-specific sequences can be added to the 5'-end of each primer. An example of a non-specific sequence is a sequence containing a restriction site. Addition of such a sequence facilitates cloning of the amplification product.

The present invention also features probes chosen from the regions amplified with primer pairs described above using the DNAstar program. Examples of the probes are as follows:

(1) human parainfluenza virus 1 probes P1-1, P1-2, P1-3, PIV1-P4, PIV1-P5, and PIV1-P6;

(2) human parainfluenza virus 2 probes P2-1, P2-2, and P2-3;

(3) human parainfluenza virus 3 probes P3-1, P3-2, and P3-3;

(4) respiratory syncytial virus probes R-1, R-2, R-3, R-10, R-4, R-71, and R-72;

(5) influenza virus A probes A1, A2, and A3;

(6) influenza virus B probes B1, B2, and B3;

(7) adenovirus probes D-1, D-2, D-3, ADV-P4, and ADV-P5.

The sequence of each probe is listed in Table 3 below in Example 3. These probes, and longer probes containing them and having 20–1000 (e.g., 20–500, 20–200, and 20–50) nucleotides in length can be used for detecting the seven viruses mentioned above by hybridizing to unamplified target virus nucleic acids or target virus nucleic acids amplified with the above-described primer pairs. For instance, the amplification products described above are examples of such longer probes. GenBank search indicates that the nucleic acid sequences amplified with the primer pairs described above are specific for each of the seven viruses. When a probe is combined with other probes for simultaneous detection of multiple viruses, the specificity of the probe should not be affected by the presence of other probes, i.e., it still hybridizes to the target virus nucleic acid. Preferably, a probe selected for one virus does not hybridize to a nucleic acid prepared from another virus.

The probes can be immobilized on the surface of a solid support, such as a membrane (a nylon-membrane or a nitrocellulose membrane), a glass, or a plastic polymer. Immobilization of probes to a membrane can be achieved by baking at 80° C. or UV cross-linking. The probes can also be covalently linked to a material (e.g., poly-lysine) coated on the surface of a glass. In addition, a novel method of immobilizing probes on a plastic polymer has recently been developed. See U.S. application Ser. No. 09/906,207. Alternatively, the probes can be synthesized de novo at precise positions on a solid substrate. See Schena et al., 1995, *Science* 270: 467; Kozal et al., 1996, *Nature Medicine* 2(7): 753; Cheng et al., 1996, *Nucleic Acids Res.* 24(2): 380; Lipshutz et al., 1995, *BioTechniques* 19(3): 442; Pease et al., 1994, *Proc. Natl. Acad. Sci. USA* 91: 5022; Fodor et al., 1993, *Nature* 364: 555; and Fodor et al., WO 92/10092.

A target amplification product described above can be detected by binding it to an immobilized probe. To facilitate detection, a labeled amplification product can be generated with a labeled amplification primer. Alternatively, the labeling can be done, chemically or enzymatically, after amplification. Examples of labeling reagents include, but are not limited to, a fluorescent molecule (e.g., fluorescein and rhodamine), a radioactive isotope (e.g., $^{32}P$ and $^{125}I$), a calorimetric reagent, and a chemiluminescent reagent. Biotin and digoxgenin are frequently used for colorimetric detection on a membrane or a plastic polymer. Fluorescent labels, such as Cy3 and Cy5, are widely used for detection on a glass. In addition, artificial tagging tails (e.g., a protein or its antibody) can be conjugated to the 5'-end of the primers or either end of the probes. See Stetsenko and Gait, 2000, *J. Org. Chem.* 65(16): 4900.

The specificity of the virus detection method of this invention is unexpectedly high. When primer pairs specific for different viruses are mixed together for simultaneous detection of the viruses, each virus nucleic acid template is only amplified with a primer pair selected for that particular virus. There is no non-specific amplification caused by the presence of other primer pairs. Likewise, when probes specific for different viruses are mixed together for simultaneous detection of the viruses, each target virus nucleic acid only hybridizes to a probe selected for that particular virus. There is no non-specific hybridization between a target virus nucleic acid and probes selected for other viruses.

Also within the scope of this invention is use of the above-described sequences specific for the seven viruses in combination with other species-specific nucleic acid sequences for simultaneous identification of even more microorganisms.

Furthermore, at positions where single nucleotide polymorphisms occur, nucleotide variations are allowed in primers and probes described in this invention. As single nucleotide polymorphisms may be associated with a particular genotype or phenotype, these primers and probes can be used to distinguish and categorize different virus strains.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

EXAMPLE 1

Amplification and Detection of a Specific Respiratory Virus

A. Design of Primers (1) Human Parainfluenza Virus 1 (HPIV 1) Primers

HPIV 1 sequences from GenBank Accession Nos u01075, af016281, m31228, m86780, m86781, m86783, m86785, m86787, m86791, m91648, u01073, u01074, af016280, u70948u01079, u01081, u01083, u01085, u70936, u10938, u70940, u70942, u70944, u70946, and u01077 were analyzed using the DNAstar program. A conserved region was identified in the hemagglutinin-neuraminidase (HN) gene area. Two forward primers (PIV1-f834 and PIV1-f849) and two reverse primers (PIV1-r1049 and PIV1-r1099) were selected from this conserved region (Table 1).

(2) Human Parainfluenza Virus 2 (HPIV 2) Primers

HPIV 2 sequences from GenBank Accession Nos af039930, af039931, af039932, af039934, af039937, x57559, af213353, af213354, d00865, and af213352 were analyzed using the DNAstar program. A conserved region was identified in the HN gene area. Two forward primers (PIV2-f929 and PIV2-f1015) and one reverse primer (PIV2-r1182) were selected from this conserved region (Table 1).

(3) Human Parainfluenza Virus 3 (HPIV 3) Primers

HPIV 3 sequences from GenBank Accession Nos Z26532, L25350, M17641, M18759, M18760, M18761, M18762, M18763, M18764, M20402, M21649,NC_001796, U51116, Z11575, aB012132, af039922, AF039924, AF039925, AF039926, AF039927, AF039929, AF039933, and AF039936 were analyzed using the DNAstar program. A conserved region was identified in the HN gene area. Two forward primers (PIV3-f774 and PIV3-f904) and two reverse primers (PIV3-r960 and PIV3-r1059) were selected from this conserved region (Table 1).

(4) Respiratory Syncytial Virus (RSV) Primers

RSV sequences from GenBank Accession Nos af035006, 63644, 50362, 50363, 11486, 74568, C_001803, 39661, 39662, 00001, f013255, C_001781, F013254, and 00736 were analyzed using the DNAstar program. A conserved region was identified in the non-structural protein 2 (NS 2) gene area. Two forward primers (RSV-f417 and RSV-fl 351) and two reverse primers (RSV-r641 and RSV-r1540) were selected from this conserved region (Table 1).

(5) Influenza Virus A (INF A) Primers

INF A sequences from GenBank Accession Nos m12594, k00576, m12592, m12590, d30673, j02150, x52146, u08862, u65674, and u65670 were analyzed using the DNAstar program. A conserved region was identified in the non-structural protein (NS) gene area. Two forward primers (INFA-f1 and INFA-f2) and two reverse primers (INFA-r1 and INFA-r2) were selected from this conserved region (Table 1).

(6) Influenza Virus B (INF B) Primers

INF B sequences from GenBank Accession Nos x13552, x00897, m18384, u70384, x13550, af101071, m58422, m58421, m65170, and k02713 were analyzed using the DNAstar program. A conserved region was identified in the hemagglutinin protein (HA) gene area. Two forward primers (INFB-92f and INFB-540f) and two reverse primers (INFB-384r and INFB-820r) were selected from this conserved region (Table 1).

(7) Adenovirus (ADV) Primers

ADV sequences from GenBank Accession Nos x67709, ab053166, x76549, x84646, af065066, j01917, and j01966 were analyzed using the DNAstar program. A conserved region was identified in the Hexon protein (Hex) gene area. Two forward primers (ADV-f1 and ADV-f2) and two reverse primers (ADV-r1 and ADV-r2) were selected from this conserved region (Table 1).

TABLE 1

| Primer sequences | |
|---|---|
| PIV1-f834<br>5'-CTGTAATAGCTGCAGGAACAAG-3' | (SEQ ID NO:1) |
| PIV1-f849<br>5'-ACAAGGGGTTATCAGTTATGCTC-3' | (SEQ ID NO:2) |
| PIV1-r1049<br>5'-TTCAATYTTTATCCCRCTTCCTAC-3' | (SEQ ID NO:3) |
| PIV1-r1099<br>5'-CCTTGGAGCGGAGTTGTTA-3' | (SEQ ID NO:4) |
| PIV2-f929<br>5'-GCTGTTCAGTCACTGCTATACC-3' | (SEQ ID NO:5) |
| PIV2-f1015<br>5'-GATCTAGCTGAACTGAGACTTGC-3' | (SEQ ID NO:6) |
| PIV2-r1182<br>5'-TATGAGACCACCATATACAGGAAA-3' | (SEQ ID NO:7) |
| PIV3-f774<br>5'-CTGTAAACTCAGACTTGGTACCTG-3' | (SEQ ID NO:8) |
| PIV3-f904<br>5'-AGTTGATGAAAGATCAGATTATGC-3' | (SEQ ID NO:9) |
| PIV3-r960<br>5'-ATATCAAGTACAATATCTTCTATGCC-3' | (SEQ ID NO:10) |
| PIV3-r1059<br>5'-CCTGGTCCAACAGATGGGTAT-3' | (SEQ ID NO:11) |
| RSV-f417<br>5'-GYATTGGCATTAAGCCTACAA-3' | (SEQ ID NO:12) |
| RSV-f1351<br>5'-GGATTGTTTATGAATGCCTATGGT-3' | (SEQ ID NO:13) |
| RSV-r641<br>5'-AACTTGACTTTGCTAAGAGCCAT-3' | (SEQ ID NO:14) |
| RSV-r1540<br>5'-TTGGRTTGTTCAATATATGGTAGA-3' | (SEQ ID NO:15) |
| INFA-f1<br>5'-CACTTAAAATGACCATGGCCTC-3' | (SEQ ID NO:16) |
| INFA-f2<br>5'-CGAAATTTCACCATTGCCTTC-3' | (SEQ ID NO:17) |
| INFA-r1<br>5'-GAAGGCTTAGGTGAAATTTCGC-3' | (SEQ ID NO:18) |
| INFA-r2<br>5'-GTCTCACTTCTTCAATCAGCCA-3' | (SEQ ID NO:19) |
| INFB-92f<br>5'-CTGGGATAACATCKTCAAACTC-3' | (SEQ ID NO:20) |
| INFB-540f<br>5'-AACAATGGCTTGGGCTG-3' | (SEQ ID NO:21) |
| INFB-384r<br>5'-TGTTCTGTCGTGCATTATAGG-3' | (SEQ ID NO:22) |
| INFB-820r | |

TABLE 1-continued

| Primer sequences | |
|---|---|
| 5'-CAACAATTCTRCCGCTTT-3' | (SEQ ID NO:23) |
| ADV-f1<br>5'-CCACCTTCTTCCCCAT-3' | (SEQ ID NO:24) |
| ADV-f2<br>5'-AACATGACCAARGACTGGT-3' | (SEQ ID NO:25) |
| ADV-r1<br>5'-CTCATKGGCTGGAAGTT-3' | (SEQ ID NO:26) |
| ADV-r2<br>5'-GAACCAGTCYTTGGTCATGT-3' | (SEQ ID NO:27) |

B. Preparation of a Virus Culture

Clinical samples were kindly provided by Dr. Shin-Ru-Shih (Chang Gung University, Tao Yuan, Taiwan): HPIV 1 (sample numbers 580 and 4056), HPIV 2 (sample numbers 4855 and 5088), HPIV 3 (sample numbers 3116 and 3229), RSV (sample numbers 3116 and 3229), INF A (sample numbers NSW, PC, and DR), INF B (sample numbers 95, 96, 97, 98, 01), and ADV (sample numbers 5456, 608, and 819).

Throat swab specimens were collected from patients showing symptoms of virus infection, and were transferred to Hank's solution containing 0.2% BPA (p-borono-L-phenylalanine), 100 units of penicillin, 100 μg streptomycin, and 1.25 μg fungizone. Samples were kept at room temperature for 0.5–3 hours in emergency room before refrigerated at 4° C. or −80° C.

Monkey Kidney-2 cells were cultivated in a cell culture medium containing 2% FBS-MEM, 100 units of penicillin, 100 μg streptomycin, and 1.25 μg fungizone. Clinical specimens, 100 μl each, were inoculated into the cell culture medium and were incubated at 37□, with $CO_2$, for 7–10 days.

C. Nucleic Acid Extraction and RT-PCR

Virus culture was centrifuged. Nucleic acids were isolated from 50 μl of the supernatant using the High Pure Viral Nucleic Acid Purification Kit (Roche), and were suspended in 20 μl DEPC-treated $H_2O$.

Two microliters of the nucleic acid solution were mixed with 1 μl of random primers $Pd(N)_6$ (Roche, 5 μg/μl). The mixture was incubated at 72□ for 10 min, and was stored at 4 □.

The Ready-To-Go RT-PCR Beads (Amersham Pharmacia Biotech Inc., U.S.A.) was dissolved in 35 μl DEPC-treated $H_2O$. 7 μl of the solution were added to the pretreated nucleic acid mixture described above. The final mixture was incubated at 42□ for 45 min. Note that ADV is a DNA virus, thus the reverse transcription is not applicable.

Each PCR tube contained 1 μl of 10X Taq DNA polymerase buffer, 0.3 μl of 25 mM $MgCl_2$, 0.8 μl of 2.5 mM dNTPs (Promega, Madison, Wis., U.S.A.), 0.2 μl of 100 μM forward primer, 0.2 μl of 100 M reverse primer, 0.2 μl formamide, 5 μl of reverse transcription mixture, and 0.1 μl Taq DNA polymerase (5 units/μl). $dH_2O$ was added to the mixture to bring the final volume to 10 μl.

Amplification was carried out using Peltier-effect Thermal Cyclers (PTC-100, MJ Research Inc., MA, U.S.A.) as follows: 95□ for 5 min; 35 cycles of 95□ for 40 sec, 50□ for 40 sec, and 72□ for 40 sec; and a final extension at 72□ for 5 min.

D. Detection of Amplification Products

Five microliters of amplified products were analyzed by electrophoresis on a 2% agarose gel in TAE buffer (Tris- HCl, pH 8.0, 1 mM EDTA). Amplification products were detected by staining the agarose gel with ethidium bromide.

Unexpectedly, specific amplification products were detected as follows:

(1) HPIV 1: a218 bp fragment from amplification with primer set f834 and r1049, a 201 bp fragment from amplification with primer set f849 and r1049, and a 268 bp fragment from amplification with primer set f834 and r1099. Amplification with primer set f849 and r1099 produced a 251 bp non-specific fragment.

(2) HPIV 2: a 254 bp fragment from amplification with primer set f929 and r1182, and a 168 bp fragment from amplification with primer set f1015 and r1182.

(3) HPIV 3: a 187 bp fragment from amplification with primer set f774 and r960, a 286 bp fragment from amplification with primer set f774 and r1059, and a 156 bp fragment from amplification with primer set f904 and r1059. Amplification with primer set f904 and r960 failed to produce a 57 bp fragment.

(4) RSV: a 222 bp fragment from amplification with primer set f417 and r641, and a 194 bp fragment from amplification with primer set f1351 and r1540.

(5) INF A: a 268 bp fragment from amplification with primer set INFA-f1 and INFA-r1, a 252 bp fragment from amplification with primer set INFA-f2 and INFA-r2, and a 499 bp fragment from amplification with primer set INFA-f1 and INFA-r2.

(6) INF B: a 293 bp fragment from amplification with primer set 92f and 384r, and a 275 bp fragment from amplification with primer set 540f and 820r. However, the 275 bp band is not as strong as the 293 bp band.

(7) ADV: a 556 bp fragment from amplification with primer set ADV-f1 and ADV-r1, a 449 bp fragment from amplification with primer set ADV-f1 and ADV-r2, and a 128 bp fragment from amplification with primer set ADV-f2 and ADV-r1.

EXAMPLE 2

Simultaneous Detection of Seven Respiratory Viruses on an Agarose Gel

Clinical samples used in this example were PIV 1 number 580, PIV2 number 5129, PIV3 number 1057, RSV number 3167, INF A number DR, INF B number 01, and ADV number 5456, provided by Dr. Shin-Ru-Shih (Chang Gung University, Tao Yuan, Taiwan).

All steps were carried out as described in Example 1, except that an oligo-nucleotide primer mixture was used for amplification instead of a single pair of primers. The oligo-nucleotide primer mixture contained seven pairs of primers, one for each of the seven viruses (Table 2). The final concentration of each primer was 1 μM.

TABLE 2

| Primers used for muliplex PCR | |
|---|---|
| PIV1-f834<br>5'-CTGTAATAGCTGCAGGAACAAG-3' | (SEQ ID NO:1) |
| PIV1-r1099<br>5'-CCTTGGAGCGGAGTTGTTA-3' | (SEQ ID NO:4) |
| PIV2-f1015<br>5'-GATCTAGCTGAACTGAGACTTGC-3' | (SEQ ID NO:6) |

TABLE 2-continued

| Primers used for muliplex PCR | |
|---|---|
| PIV2-r1182<br>5'-TATGAGACCACCATATACAGGAAA-3' | (SEQ ID NO:7) |
| PIV3-f904<br>5'-AGTTGATGAAAGATCAGATTATGC-3' | (SEQ ID NO:9) |
| PIV3-r1059<br>5'-CCTGGTCCAACAGATGGGTAT-3' | (SEQ ID NO:11) |
| RSV-f417<br>5'-GYATTGGCATTAAGCCTACAA-3' | (SEQ ID NO:12) |
| RSV-r641<br>5'-AACTTGACTTTGCTAAGAGCCAT-3' | (SEQ ID NO:14) |
| INFA-f2<br>5'-CGAAATTTCACCATTGCCTTC-3' | (SEQ ID NO:17) |
| INFA-r2<br>5'-GTCTCACTTCTTCAATCAGCCA-3' | (SEQ ID NO:19) |
| INFB-92f<br>5'-CTGGGATAACATCKTCAAACTC-3' | (SEQ ID NO:20) |
| INFB-384r<br>5'-TGTTCTGTCGTGCATTATAGG-3' | (SEQ ID NO:22) |
| ADV-f1<br>5'-CCACCTTCTTCCCCAT-3' | (SEQ ID NO:24) |
| ADV-r1<br>5'-CTCATKGGCTGGAAGTT-3' | (SEQ ID NO:26) |

Unexpectedly, a specific amplification product was detected in each sample, i.e., (1) a 268 bp fragment from amplification of the HPIV 1 template with primer set f834 and r1099, (2) a 168 bp fragment from amplification of the HPIV 2 template with primer set f1015 and r1182f, (3) a 156 bp fragment from amplification of the HPIV 2 template with primer set f904 and r1059, (4) a 222 bp fragment from amplification of the RSV template with primer set f417 and r641, (5) a 252 bp fragment from amplification of the INF A template with primer set INFA-12 and INFA-r2, (6) a 293 bp fragment from amplification of the INF B template with primer set 92f and 84r, and (7) a 556 bp fragment from amplification of the ADV template with primer set ADV-f1 and ADV-r1.

EXAMPLE 3

Simultaneous Detection of Seven Respiratory Viruses on an Array Chip

Sample preparation and RT-PCR were carried out as described in Example 2, except that all primers were labeled with biotin at the 5'-end. Amplification products were detected on an array chip described below.

A. Design of Probes

Probes were selected from the amplified region of each virus genome using the DNAstar program (Table 3).

TABLE 3

Probe sequences

HPIV 1 probes

| | | |
|---|---|---|
| P1-1 | 5'-CTCCYTGCCYACTGTRAATGAGACTA-3' | (SEQ ID NO:28) |
| P1-2 | 5'-CGAGTGAAGGTATAGAAGAYTTAGTATTTGACA-3' | (SEQ ID NO:29) |
| P1-3 | 5'-CTCAAGGGAAAGACCAAATCTCATCG-3' | (SEQ ID NO:30) |
| PIV1-P4 | 5'-GCTGCAGGAACAAGGGGTTATCAGTTATGC-3' | (SEQ ID NO:31) |
| PIV1-P5 | 5'-GTGTAGGAAGRGGGATAAAYATTGAA-3' | (SEQ ID NO:32) |
| PIV1-P6 | 5'-CCTTGGAGCGGAGTTGTTAAGCCACCG-3' | (SEQ ID NO:33) |

HPIV 2 probes

| | | |
|---|---|---|
| P2-1 | 5'-GATCTAGCTGAACTGAGACTTGCTTTCTATTATTAT-3' | (SEQ ID NO:34) |
| P2-2 | 5'-TCATATCTCTTCCAAAYACAACAGGGCA-3' | (SEQ ID NO:35) |
| P2-3 | 5'-TGCAGTYGGAAGCGGGATCTATC-3' | (SEQ ID NO:36) |

HPIV 3 probes

| | | |
|---|---|---|
| P3-1 | 5'-TGCATCATCAGGCATAGAAGATATTGTAC-3' | (SEQ ID NO:37) |
| P3-2 | 5'-ATYATGATGGYTCAATCTCAACAACAAG-3' | (SEQ ID NO:38) |
| P3-3 | 5'-ATCTCAACAACAAGATTTAAGAAYAATAAYATAA-3' | (SEQ ID NO:39) |

RSV probes

| | | |
|---|---|---|
| R-1 (RSV A) | 5'-TAAGCCTACAAAGCAYACTCCCATAATA-3' | (SEQ ID NO:40) |
| R-2 (RSV B) | 5'-AAATATGACCTCAACCCGTAAATTCCAA-3' | (SEQ ID NO:41) |
| R-3 (RSV B) | 5'-AACCCAWCCAAACYAAGCTATTCC-3' | (SEQ ID NO:42) |
| R-10 (RSV A) | 5'-GATGGAGCCTGAAAATTATAGTAATTTAAAATTAAGGAG-3' | (SEQ ID NO:43) |
| R-4 (RSV B) | 5'-CAAACAACARTGCTCAAYAGTTAAGAAGGA-3' | (SEQ ID NO:44) |
| R-71 (RSV A) | 5'-AGGAGAGATATAAGATGAAAGATGGGGC-3' | (SEQ ID NO:45) |
| R-72 (RSV A) | 5'-AGGAGAGACATAAGATAGAAGATGGGGC-3' | (SEQ ID NO:46) |

INF A probes

| | | |
|---|---|---|
| A1 | 5'-CGGAGGACTTGAATGGARTGATAACAC-3' | (SEQ ID NO:47) |
| A2 | 5'-TCTACAGAGATTCGCTTGGRGAAGCAG-3' | (SEQ ID NO:48) |
| A3 | 5'-GACMTCCACTYACTCCAAAACAGAAAC-3' | (SEQ ID NO:49) |

INF B probes

| | | |
|---|---|---|
| B1 | 5'-TGTGATACCACTGACAACAACACCWAC-3' | (SEQ ID NO:50) |
| B2 | 5'-GCAAATCTCAAAGGAACAAARACYAG-3' | (SEQ ID NO:51) |
| B3 | 5'-AAACTATGCCCAAMSTGTYTCAACTGY-3' | (SEQ ID NO:52) |

ADV probes

| | | |
|---|---|---|
| D-1 | 5'-TCCCCATGGCBCACAACACNGC-3' | (SEQ ID NO:53) |
| D-2 | 5'-TCKCGCAACTGGGCRGCYTT-3' | (SEQ ID NO:54) |
| D-3 | 5'-AACCACACYTTYAAGAAGGTSKCCATC-3' | (SEQ ID NO:55) |
| ADV-P4 | 5'-AACATGACCAARGACTGGTTCCTGGT-3' | (SEQ ID NO:56) |
| ADV-P5 | 5'-TACAAYATYGGMTACCAGGGCTTYTA-3' | (SEQ ID NO:57) |

B. Spotting and Hybridization

Probes were spotted on a DR. Polymer™ Chip. Additional 5 to 20-mers of poly-T were attached to each of the probes before spotting. The probes were UV cross-linked to the surface of a DR. Polymer™ Chip. 4 positive detection controls, 4 positive PCR controls, 4 positive hybridization controls, and 4 negative controls were also spotted on the polymer chip.

Prior to hybridization, 8 µl of PCR products were denatured for 5 minutes and mixed with 392 µl of DR. Hyb™ Hybridization Buffer-E. The mixture was added to the DR. Polymer™ Chip in a hybridization chamber and incubated at 50° C. for 1 hour. The chip was subsequently washed with 500 µl DR. Wash Buffer 5 times.

C. Detection

Four hundred microliters of DR. Block Buffer were mixed with 0.2 µl streptavidin-AP (alkaline phosphatase). The mixture was added to the DR. Polymer™ Chip in a hybridization chamber, and was incubated for 30 minutes at room temperature. The chip was subsequently washed with DR. Wash Buffer 5 times.

Three hundred and ninety-two microliters of DR. Detection Buffer were mixed with 8 µl NBT/BCIP. The mixture was added to the DR. Polymer™ Chip in a hybridization chamber, and was incubated for 10 minutes in a dark room. The chip was subsequently washed twice with DR. Wash Buffer prior to color development.

Unexpectedly, each probe specifically designed for a particular virus was able to capture the amplification product produced from the template isolated from the target virus sample, i.e., (1) color developed at P1-1, P1-2, P1-3, PIV1-P4, PIV1-P5, and PIV1-P6 spots when the probes were hybridized to HPIV 1 amplification products; (2) color developed at P2-1P2-2, and P2-3 spots when the probes were hybridized to HPIV 2 amplification products; (3) color developed at P3-1, P3-2, and P3-3 spots when the probes were hybridized to HPIV 3 amplification products; (4) color developed at R-1, R-2, R-3, R-10, R-4, and a mixture of R-71 and R-72 spots when the probes were hybridized to RSV amplification products; (5) color developed at A1, A2, and A3 spots when the probes were hybridized to INF A amplification products; (6) color developed at B1, B2, and B3 spots when the probes were hybridized to INF B amplification products; and (7) color developed at D-1, D-2, D-3, ADV-P4, and ADV-P5 spots when the probes were hybridized to ADV amplification products.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A set of nucleic acids comprising:

a first pair of primers, both containing oligo-nucleotides selected from the hemagglutinin-neuraminidase gene region of human parainfluenza virus 2, and the oligo-nucleotides in the first pair of primers being, respectively, SEQ ID NOs:5 and 7, or SEQ ID NOs:6 and 7;

a second pair of primers, both containing oligo-nucleotides selected from the hexon gene region of adenovirus, the oligo-nucleotides in the second pair of primers being, respectively, SEQ ID NQs:24 and 26, SEQ ID NOs:24 and 27, or SEQ ID NOs:25 and 27; and a third pair of primers, both containing oligo-nucleotides selected from the non-structural protein 2 gene region of respiratory syncytial virus, the oligo-nucleotides in the third pair of primers being, respectively, SEQ ID NOs:12 and 14, or SEQ ID NOs:13 and 15, wherein each nucleic acid is 14–40 nucleotides in length, and each primer is a single compound.

2. The set of nucleic acids of claim 1, further comprising:

a fourth pair of primers containing, respectively, oligo-nucleotides SEQ ID NOs:1 and 3, SEQ ID NOs:2 and 3, or SEQ ID NOs:1 and 4;

a fifth pair of primers containing, respectively, oligo-nucleotides SEQ ID NOs:8 and 10, SEQ ID NOs:8 and 11, or SEQ ID NOs:9 and 11;

a sixth pair of primers containing, respectively, oligo-nucleotides SEQ ID NOs:16 and 18, or SEQ ID NOs:17 and 19; or a seventh pair of primers containing, respectively, oligo-nucleotides SEQ ID NO:20 and 22, or SEQ ID NOs:21 and 23, or a combination thereof.

3. A set of nucleic acids comprising:

a first nucleic acid containing a first oligo-nucleotide selected from the non-structural protein 2 gene region of respiratory syncytial virus;

a second nucleic acid containing a second oligo-nucleotide selected from the hemagglutinin gene region of influenza virus B; and a third nucleic acid containing a third oligo-nucleotide selected from the non-structural protein gene region of influenza virus A, wherein each oligo-nucleotide is a single compound selected from the group consisting of SEQ ID NOs:40–52 and sequences complementary thereto, and each nucleic acid is 20–200 nucleotides in length.

4. The set of nucleic acids of claim 3, wherein each nucleic acid has 20–50 nucleotides in length.

5. The set of nucleic acids of claim 3, further comprising a nucleic acid containing an oligo-nucleotide selected from the group consisting of SEQ ID NQs:28–39, 53–57, and sequences complementary thereto, wherein each nucleic acid has 20–200 nucleotides in length.

6. The set of nucleic acids of claim 5, wherein each nucleic acid has 20–50 nucleotides in length.

* * * * *